(12) United States Patent
Liu

(10) Patent No.: US 10,028,756 B2
(45) Date of Patent: Jul. 24, 2018

(54) PATIENT-SPECIFIC ACCETABULAR GUIDE

(71) Applicant: Shanghai Xinjian Medical Co. LTD, Shanghai (CN)

(72) Inventor: Fei Liu, Shanghai (CN)

(73) Assignee: Shanghai Xinjian Medical Co. LTD, Shanghai (CN)

( * ) Notice: Subject to any disclaimer, the term of this patent is extended or adjusted under 35 U.S.C. 154(b) by 284 days.

(21) Appl. No.: 15/068,685

(22) Filed: Mar. 14, 2016

(65) Prior Publication Data
US 2017/0258480 A1    Sep. 14, 2017

(51) Int. Cl.
*A61B 17/17* (2006.01)
*A61B 34/10* (2016.01)
*A61B 17/16* (2006.01)

(52) U.S. Cl.
CPC ...... *A61B 17/1746* (2013.01); *A61B 17/1666* (2013.01); *A61B 2034/108* (2016.02)

(58) Field of Classification Search
CPC ............ A61B 17/1746; A61B 17/1666; A61B 2034/108
See application file for complete search history.

(56) References Cited

U.S. PATENT DOCUMENTS

| 8,603,180 | B2 | 12/2013 | White |
| 8,608,749 | B2 | 12/2013 | Meridew |
| 8,808,186 | B2 * | 8/2014 | Fruland ............... A61B 5/0066 600/459 |
| 2010/0023015 | A1 * | 1/2010 | Park ...................... A61B 17/15 606/87 |
| 2010/0274253 | A1 * | 10/2010 | Ure .................... A61B 17/1746 606/91 |
| 2011/0190775 | A1 | 8/2011 | Ure |
| 2014/0316416 | A1 | 10/2014 | Liu |

* cited by examiner

*Primary Examiner* — Christian Sevilla
(74) *Attorney, Agent, or Firm* — Andrew C. Cheng

(57) ABSTRACT

A patient-specific acetabular guide comprises a cup body, a plurality of alignment arms extending from the cup body and engaging periacetabular areas of a pelvis, and a supporting leg protruding from the cup body and abutting against a portion of an acetabular fossa. Each alignment arm has a fixing hole extending inclinedly therethrough to allow a Kirschner pin to pass through and enter the periacetabluar area of the pelvis for positing and orienting the acetabular guide on a predetermined location of an acetabulum.

13 Claims, 5 Drawing Sheets

PATIENT-SPECIFIC ACCETABULAR GUIDE

BACKGROUND OF THE INVENTION

1. Field of the Invention

The present invention relates to a patient-specific acetabular guide, and more particularly to a patient-specific acetabular guide used in a hip-joint replacement surgery and method of manufacturing the same. The patient-specific acetabular guide can be used in connection with various other instruments to facilitate guided reaming procedure of an acetabulum of a pelvis of a specific patient and a guided procedure of insertion and implantation of an acetabulum implant or acetabular cup in the acetabulum.

2. Description of the Prior Art

A conventional patient-specific acetabular guide disclosed in U.S. Pat. No. 8,608,749 issued to Meridew et al. on Dec. 17, 2013 comprises a patient-specific body covering the acetabular fossa at the center of the acetabulum and a guiding element having an elongated bore with a patient-specific alignment axis configured to be central to the acetabular cup and perpendicular to the acetabular cup's surface when the acetabular guide is positioned to the acetabulum. The elongated bore of the guiding element is used for leading a tool to drill the acetabulum along the patient-specific alignment axis.

The acetabular guide also includes two marker elements each having an elongated bore for guiding marker pin. The marker pins are used for supporting a secondary guide which is used to adjust the orientation and position of the acetabular cup when the acetabular cup is placed onto the acetabulum. The marker elements both extend upwardly from the patient-specific body. The patient-specific body designed by using a three-dimensional model of the acetabulum and surrounding pelvic area of the patient includes an inner portion from which the guiding element extends, and an outer portion extending from the inner portion and configured to extend over a portion of the acetabular rim. The inner portion is designed to engage the acetabulum. The outer portion extends sufficiently beyond the rim to the periacetabular area of the pelvis to accommodate the marker elements.

The patient-specific body also has an underside three-dimensional engagement surface that is custom-made or patient-specific to conform to and mirror complementary surface of the acetabulum, rim or other periacetabular surface of the pelvis of the specific patient. The engagement surface of the patient-specific body enables the acetabular guide to nest or closely mate relative to the complementarily acetabular surface of the patient. However, the process of placing the acetabular guide is not described and malposition of the acetabular guide is easily produced due to the hemispherical shape of the acetabular during manually placing the acetabular guide to the acetabulum of the patient.

Hence, it is desirable to provide an improved patient-specific acetabular guide and method of manufacturing the same to overcome the aforementioned disadvantages.

SUMMARY OF THE INVENTION

Accordingly, an object of the present invention is to provide a patient-specific acetabular guide for facilitating a guided reaming procedure of an acetabulum of a pelvis.

According to one aspect of the present invention, a patient-specific acetabular guide, capable of being positioned and oriented on a predetermined location of an acetabulum of a pelvis, comprises a cup body configured with a hemispherical shape, a plurality of spaced alignment arms extending from the cup body, a supporting leg protruding outwardly from the cup body, and a guiding element extending upwardly from a bottom of the cup body and defining an elongated bore extending therethrough, and wherein the elongated bore has an axis predetermined by a preoperative surgical plan.

Other objects, advantages and novel features of the present invention will become more apparent from the following detailed description when taken in conjunction with the accompanying drawings, in which:

DESCRIPTION OF PREFERRED EMBODIMENTS OF THE INVENTION

Reference is now made to the drawings to describe the invention in detail.

Figure 1:
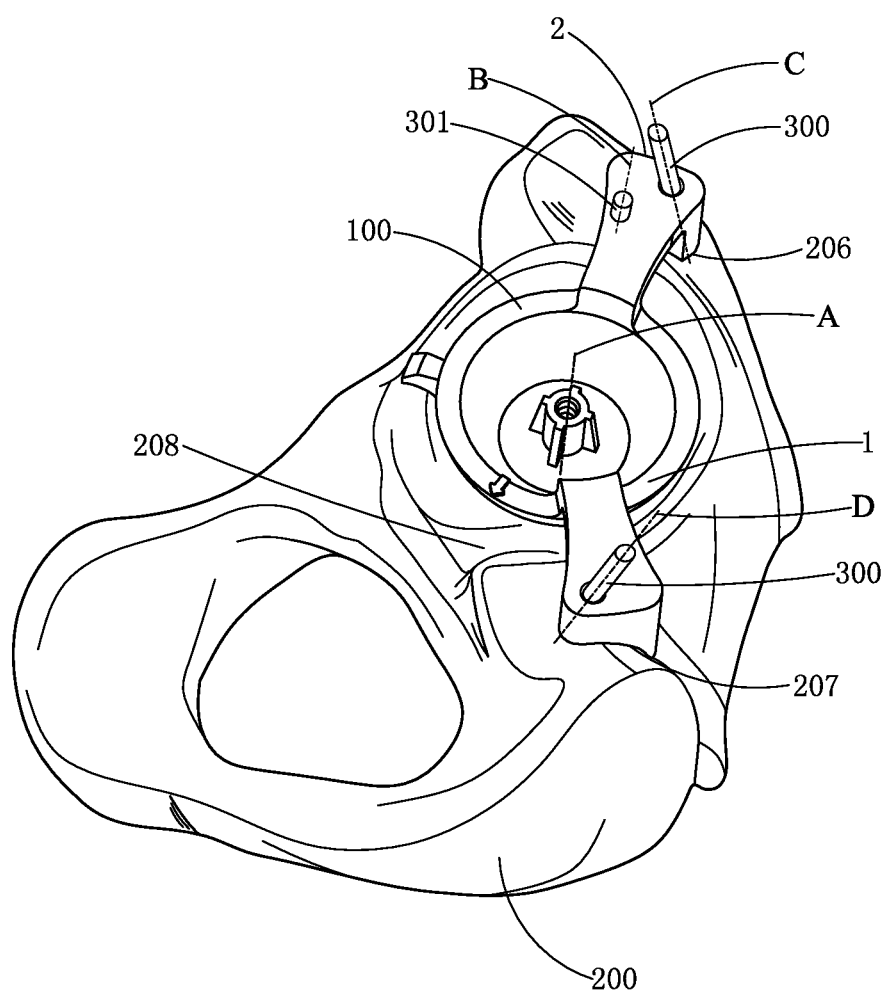
FIG. 1 is an assembled, perspective view of a patient-specific guide and an acetabulum of a specific patient in accordance with the preferred embodiment of the present invention.
Figure 2:
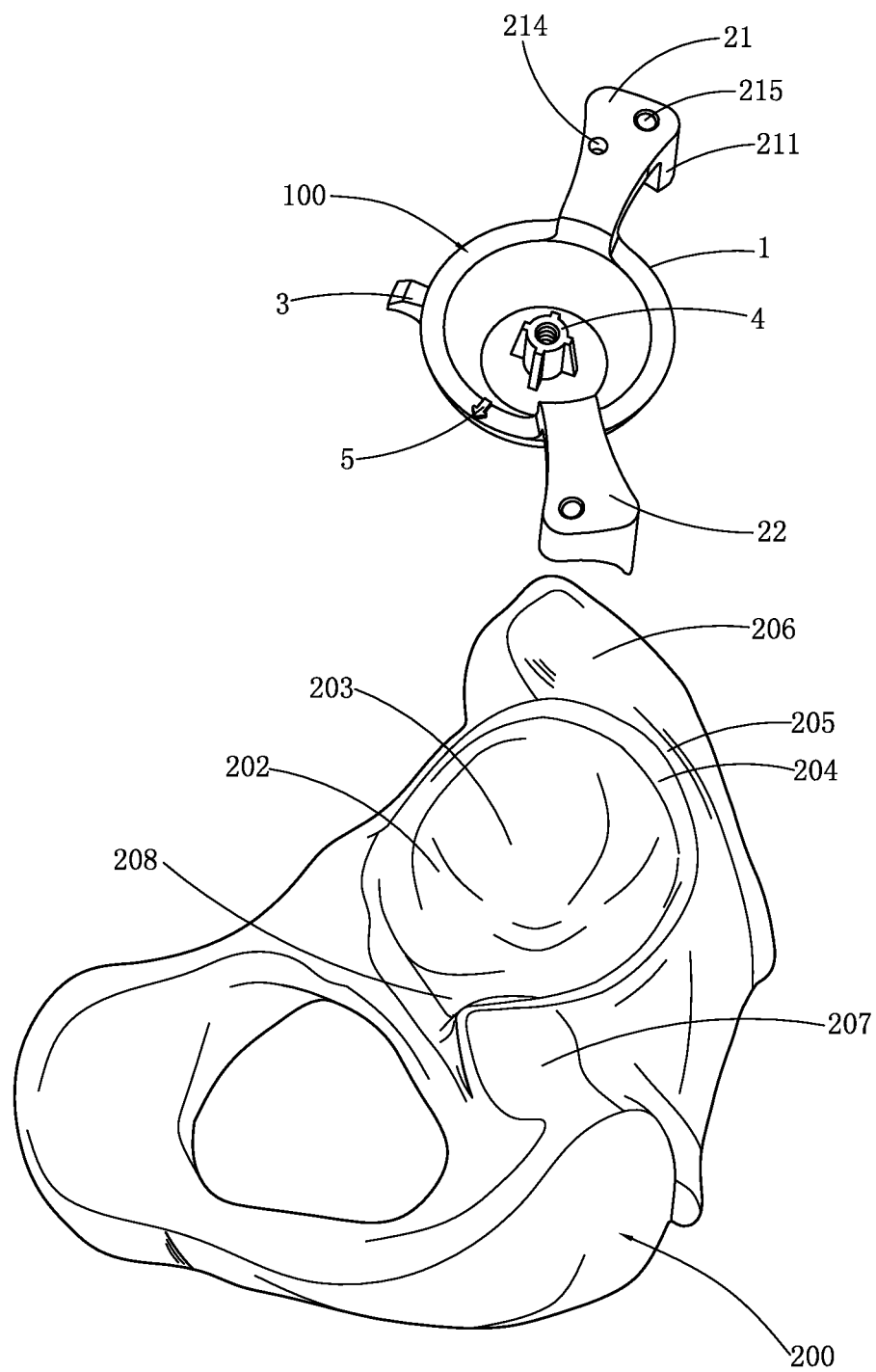
FIG. 2 is an exploded, perspective view of the patient-specific guide and an acetabulum of the specific patient shown in FIG. 1.
Figure 3:
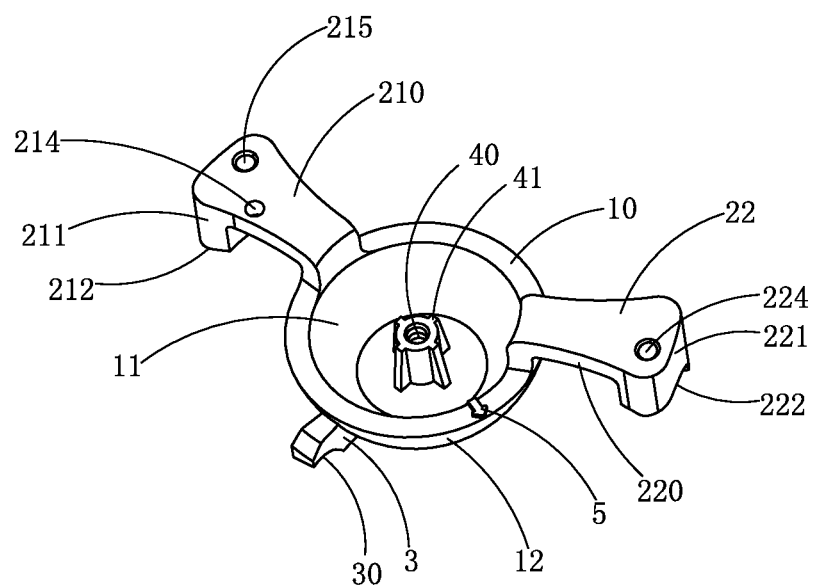
FIG. 3 is a perspective view of the patient-specific guide shown in FIG. 1.
Figure 4:
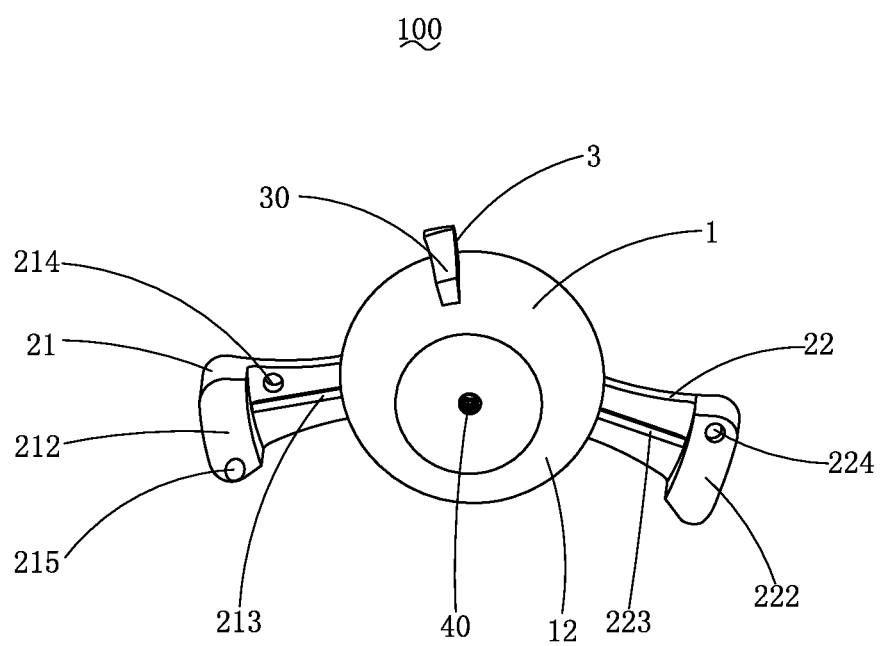
FIG. 4 is another perspective view of the patient-specific guide shown in FIG. 3.
Figure 5:
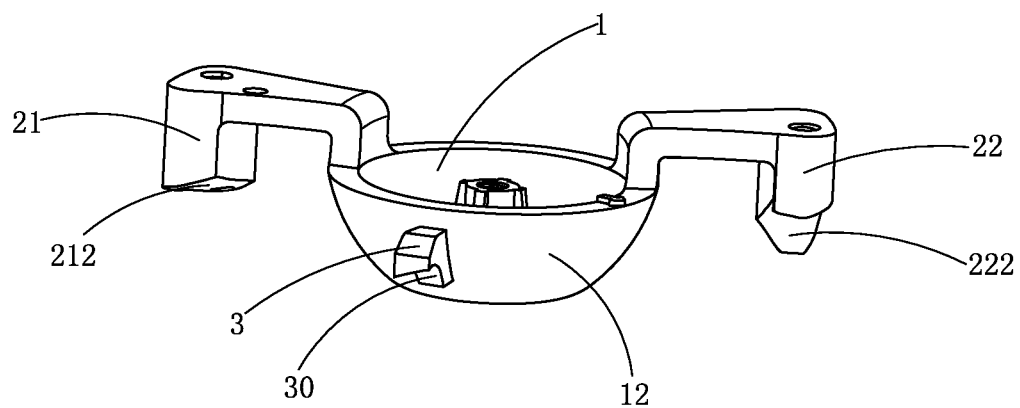
FIG. 5 is another perspective view of the patient-specific guide shown in FIG. 3.

Referring to FIGS. 1-5, a patient-specific acetabular guide 100 in accordance with a preferred embodiment of this invention is disclosed. The patient-specific acetabular guide 100 is used in connection with other instruments described in prior art for facilitating a guided reaming procedure of an acetabulum 202 of a pelvis 200 and a guided insertion and implantation procedure of an acetabular cup (not shown) in the acetabulum 202 during a hip-joint replacement surgery. The patient-specific acetabular guide 100 comprises a cup body 1 having a rim portion 10 at the top thereof, a plurality of spaced alignment arms 2 extending from the rim portion 10 of the cup body 1, and a supporting leg 3 protruding from the cup body 1. The patient-specific acetabular guide 100 is positioned and orientated on a predetermined location of the acetabulum 202 to provide an accurate alignment axis relative to the planned or predetermined orientation of the acetabular cup (not shown) through the alignment arms 2 which engages the periacetabular surface of the pelvis 200 and the supporting leg 3 which abuts against an acetabular fossa 203 of the acetabulum 202. The predetermined location of the acetabulum 202 is determined during a preoperative surgical procedure and based on a three-dimensional reconstruction of the pelvis 200 and an implanting position of the acetabular cup (not shown). The three-dimensional reconstruction can be generated based on two-dimensional medical images, including MRI, CT or X-ray scans, and later processed with commercially available imaging software.

The cup body 1 covers an acetabular fossa 203 at the center of the acetabulum 202 which provides a reference coordination for rotational stability and unique positioning on the acetabulum 202. The cup body 1 is configured to have a hemispherical shape and defines an inner surface 11 and an outer surface 12 opposite to each other. The inner and outer surfaces 11, 12 of the cup body 1 both are configured to be a hemispherical shape and are connected with each other through the rim portion 10. The cup body 1 defines a guiding element 4 extending upwardly from the bottom thereof. The guiding element 4 has an elongated bore 40 with a patient-specific alignment axis A created to serve as a central line with respect to the acetabular cup (not shown) and is perpendicular to the acetabular cup's surface when the acetabular guide 100 is positioned on the acetabulum 202. The elongated bore 40 is configured as a threaded hole and can be used with a handle (not shown) to place the patient-specific acetabular guide 100 onto the acetabulum 202.

The alignment arms 2, each being configured to extend over a corresponding portion of the acetabular rim 204 and/or the acetabular ligament 205 for positioning the guide 100 to a desired position predetermined by a preoperative surgery plan, include a first alignment arm 21 and a second alignment arm 22 arranged spaced from each other. The first alignment arm 21 includes a first arm portion 210 bending upwardly from the corresponding rim portion 10 of the cup body 1 and a contacting portion 211 arranged at the end of the first arm portion 21. The first arm portion 210 extends beyond the corresponding portion of the acetabular rim 204 along a horizontal direction. The contacting portion 211 extends downwardly from the end of the first arm portion 210 and has an engaging surface 212 at the end thereof. The engaging surface 212 can seats onto a periacetabular surface 206 of the pelvis 200. The engaging surface 212 is custom-made to conform to and mirror complementary surface of the periacetabular surface 206 of the pelvis 200.

The first alignment arm 21 also includes a reinforcing rib 213 protruding downwardly from a bottom of the first arm portion 210. The first arm portion 210 is configured to be a plate board and has a tapered dimension. The reinforcing rib 213 is formed at a central section of the bottom of the first arm portion 210 for increasing the strength of the first arm 21 to prevent the first arm 21 from being broken during service. The first arm portion 210 defines a marker aperture 214 extending from a top to a bottom thereof. The marker aperture 214 has an axis B parallel to the alignment axis A of the elongated bore 40 of the guiding element 4. The contacting portion 211 has a locating hole 215 extending therethrough. The locating hole 215 extends from a top of the contacting portion 211 to a bottom of the contacting portion 211 along an inclined direction and has an axis C inclined to the axis B of the marker aperture 214.

The second arm 22 has a structure which is similar to the first arm 21 and includes a second arm portion 220 with a touching portion 221 at a tip thereof. The second arm portion 220 extends curvilinear upwardly from the rim portion 10 of the cup body 1 and extends over the corresponding portion of the acetabular rim 204 and the acetabular ligament 205 along a horizontal direction. The touching portion 221 extends downwardly from an end of the second arm portion 220 and has a contacting surface 222 matching to a periacetabular surface 207 of the pelvis 200. The contacting surface 222 is configured as a mirror complementary surface of the periacetabular surface 207 of the pelvis 200. The second arm 22 has a stiffener 223 disposed at a bottom of the second arm portion 220. The stiffener 223 is structured as a rib and protrudes downwardly from the bottom of the second arm portion 220 to improve the strength of the second arm portion 220 for avoiding the second arm portion 220 from being broken during service.

The second arm 22 has a positioning hole 224 with an axis D inclined to the axis C of the locating hole 215 of the first arm 21. The positioning hole 224 extends inclinedly from a top of the touching portion 221 to a bottom of the touching portion 221. The axis D of the positioning hole 224 is also inclined to the axis A of the elongated bore 4 of the guiding element 4. The patient-specific acetabular guide 100 is positioned on the acetabulum 202 through Kirschner pins 300, respectively, which pass through the locating hole 215 of the first arm 21 and the positioning hole 224 of the second arm 22, and are anchored into the corresponding portions of the periacetabular area of the pelvis 200. The marker aperture 214 of the first arm 21 can guide a marker pin 301 to anchor unto the periacetabular area of the pelvis 200. The marker pin 301 is configured as a reference point during the surgery drills the acetabulum 202.

The supporting leg 3 defines an abutted surface 30 at the end thereof for engaging with a corresponding surface of the acetabular fossa 203. The abutted surface 30 is patient-specific to conform to and mirror complementary surface of the acetabular fossa 203 of the acetabulum 202. The supporting leg 3 protrudes from the outer surface 12 of the cup body 1 and is spaced from the alignment arms 2. The guiding element 4 is structured to be a conical shape and extends upwardly from the inner surface 11 of the cup body 1 along the patient-specific alignment axis A. The guiding element 4 has a plurality of reinforcement portions 41 distributed circumferentially thereon. The reinforcement portions 41 are spaced from each other and each projects outwardly from the guiding element 4. An identification portion 5 protrudes upwardly from the rim portion 10 of the cup body 1 and is configured with an arrow pointing to an acetabular notch 208 of the acetabulum 202 when the guide 100 is seated on the acetabulum 202. The identification portion 5 is used for a reference during seating the patient-specific acetabular guide 100 on the acetabulum 202 and located at a portion of the cup body 1 which is adjacent to the second arm 22.

In assembling, the patient-specific acetabular guide 100 is seated onto the acetabulum 202 of the pelvis 200 by a fixture (not shown). The patient-specific acetabular guide 100 is securely positioned and oriented on the acetabulum 202 by the Kirschner pins 300 which are anchored onto the corresponding portions of the periacetabular areas of the pelvis 200 along the locating hole 215 and the positioning hole 224 of the alignment arm 2. The engaging surface 212 of the first arm matches completely the periacetabular surface 206 of the pelvis 200 and the contacting surface 222 of the second arm 22 matches completely the periacetabular surface 207 of the pelvis 200. The abutted surface 30 of the supporting leg 3 seats properly onto the surface of the acetabular fossa 203.

Furthermore, although the present invention has been described with reference to particular embodiments, it is not to be construed as being limited thereto. Various alterations and modifications can be made to the embodiments without in any way departing from the scope or spirit of the present invention as defined in the appended claims.

What is claimed is:
1. A patient-specific acetabular guide comprising:
a cup body configured with a hemispherical shape;
a plurality of spaced alignment arms extending from the cup body;
a supporting leg protruding outwardly from the cup body; and
a guiding element extending upwardly from a bottom of the cup body and defining an elongated bore extending therethrough, the elongated bore having an axis predetermined by a preoperative surgical plan;
wherein the supporting leg has an abutted surface at an end thereof, and wherein the plurality of alignment arms that extend from the cup body include a first alignment arm and a second alignment arm separate from each other;

wherein the first alignment arm has a first arm portion defining a contacting portion at an end thereof, and wherein the second alignment arm has a second arm portion defining a touching portion at a tip thereof, and wherein the contacting portion has an engaging surface at a bottom thereof, and wherein the touching portion has a contacting surface at a bottom thereof; and wherein the contacting portion extends downwardly from the first arm portion and has a locating hole with an axis extending inclinedly therethrough.

2. The patient-specific acetabular guide of claim 1, wherein the touching portion extends downwardly from the second arm portion and has a positioning hole with an axis extending inclinedly from a top thereof to a bottom thereof.

3. The patient-specific acetabular guide of claim 2, wherein the axis of the positioning hole is inclined to the axis of the locating hole, and wherein the axis of the positioning hole is inclined to the axis of the elongated bore, and wherein the axis of the locating hole is inclined to the axis of the elongated bore.

4. The patient-specific acetabular guide of claim 1, wherein the first arm has a marker aperture with an axis extending through the first arm portion, and wherein the axis of the marker aperture is parallel to the axis of the elongated bore.

5. The patient-specific acetabular guide of claim 1, wherein the first arm portion defines a reinforcing rib protruding downwardly from a bottom thereof, and wherein the second arm includes a stiffener disposed at a bottom of the second arm portion.

6. The patient-specific acetabular guide of claim 1, wherein the guide element has a plurality of reinforcement portions protruding around thereof.

7. The patient-specific acetabular guide of claim 1, wherein an identification portion protrudes upwardly from a top portion of the cup body and is located at a portion adjacent to the second arm.

8. A patient-specific acetabular guide capable of being positioned and oriented on a predetermined location of an acetabulum of a pelvis to provide an accurate alignment axis relative to a planned orientation of an acetabular cup, the patient-specific acetabular guide comprising:
a cup body for covering an acetabular fossa of the acetabulum at a central portion of the acetabulum;
a plurality of alignment arms extending outwardly from the cup body for engaging a periacetabular surface of the pelvis;
a supporting leg protruding from the cup body and abutting against the acetabular fossa; and
a guiding element defining an elongated bore extending therethrough,
wherein the elongated bore has a patient-specific alignment axis that is central to the acetabular cup and perpendicular to a surface of the acetabular cup when the acetabular guide is positioned on the acetabulum; and
wherein the alignment arms are each configured to extend over a corresponding portion of an acetabular rim and/or an acetabular ligament for fixing the acetabular guide to the predetermined location and wherein the alignment arms include a first arm and a second arm separate from each other;
wherein the first arm extends from a top portion of the cup body and has a contacting portion at an end thereof, and wherein the second arm extends from another top portion of the cup body and defines a touching portion at an end thereof;
wherein the first arm has an engaging surface located at a bottom of the contacting portion to fit the periacetabular surface of the pelvis, and wherein the second arm has a contacting portion located at a bottom of the touching portion to fit another periacetabular surface of the pelvis, and wherein the supporting leg defines an abutted surface at en end thereof for engaging with a corresponding surface of the acetabular fossa; and
wherein first arm has a locating hole extending inclinedly from a top of the contacting portion to a bottom of the contacting portion, and wherein the second arm has a positioning hole extending inclinedly from a top of the touching portion to a bottom of the touching portion, and wherein the locating hole has an axis inclined to the axis of the elongated bore, and wherein the positioning hole has an axis inclined to the axis of the elongated bore, and wherein the axis of the locating hole is inclined to the axis of the positioning hole.

9. The patient-specific acetabular guide of claim 8, wherein the engaging surface of the first arm and the contacting surface of the second arm both are custom-made to conform to and mirror a complementary surface of the corresponding periacetabluar surface of the pelvis, and wherein the abutted surface of the supporting leg mirrors a complementary surface of the acetabular fossa.

10. The patient-specific acetabular guide of claim 8, wherein the first arm defines a marker aperture extending inclinedly therethrough and wherein the marker aperture is separate from the locating hole, and wherein the marker aperture defines an axis parallel to the axis of the elongated bore.

11. The patient-specific acetabular guide of claim 8, wherein the first arm includes a reinforcing rib located at a bottom thereof, and wherein the second arm has a stiffener protruding downwardly from a bottom thereof.

12. The patient-specific acetabular guide of claim 8, wherein an identification portion protrudes from a top portion of the cup body and is configured with an arrow shape to point to an acetabular notch of the acetabulum when the patient-specific acetabular guide is fixed on the acetabulum.

13. The patient-specific acetabular guide of claim 12, wherein the identification portion is located at a portion of the cup body which is adjacent to the second arm.

* * * * *